United States Patent
Roberts et al.

(10) Patent No.: US 6,485,451 B1
(45) Date of Patent: Nov. 26, 2002

(54) BODY CAVITY IRRIGATION SYSTEM

(75) Inventors: Christopher R. Roberts, Skaneateles, NY (US); Michael McMahon, Syracuse, NY (US); Steven R. Slawson, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 98 days.

(21) Appl. No.: 09/630,884

(22) Filed: Aug. 2, 2000

(51) Int. Cl.[7] ................................ A61M 1/00; A61M 37/00
(52) U.S. Cl. ........................ 604/35; 604/131; 236/101 C
(58) Field of Search ............................ 604/35, 38, 27, 604/131, 150; 601/155; 236/87, 90, 101 C

(56) References Cited

U.S. PATENT DOCUMENTS

| | | |
|---|---|---|
| 605,178 A | 6/1898 | Ferguson |
| 785,524 A | 3/1905 | Shea |
| 989,839 A | 4/1911 | Fowler |
| 1,719,152 A | 7/1929 | Watson |
| 2,112,145 A | 3/1938 | Courtney |
| 2,208,031 A | 7/1940 | Hooper |
| 2,525,419 A | 10/1950 | Mellinger et al. |
| 2,626,524 A | 1/1953 | Harman |
| 2,645,116 A | 7/1953 | Baxter |
| 3,142,297 A | 7/1964 | Attebery |
| 3,669,101 A | 6/1972 | Kleiner |
| 3,682,176 A | 8/1972 | Kelson |
| 3,696,996 A | 10/1972 | Lloyd et al. |
| 3,709,204 A * | 1/1973 | Noponen |
| 3,769,976 A | 11/1973 | Victory |
| 3,782,349 A * | 1/1974 | Kamo et al. |
| 3,788,305 A | 1/1974 | Schreiber |
| 3,916,895 A | 11/1975 | Davis, Jr. |
| 3,971,375 A | 7/1976 | Hill |
| 4,149,315 A | 4/1979 | Page, Jr. et al. |
| 4,203,026 A * | 5/1980 | Walter et al. |
| 4,206,756 A | 6/1980 | Grossan |
| 4,239,177 A * | 12/1980 | Williams et al. |
| 4,258,714 A | 3/1981 | Leopoldi et al. |
| 4,282,867 A | 8/1981 | Dutoit |
| 4,284,078 A | 8/1981 | Pace |
| 4,303,195 A | 12/1981 | Hashimoto et al. |
| 4,413,633 A | 11/1983 | Yanda |
| 4,893,634 A | 1/1990 | Kulik et al. |
| 4,957,483 A | 9/1990 | Gonser et al. |
| 5,024,378 A | 6/1991 | Bergmann et al. |
| 5,241,714 A | 9/1993 | Barry |
| D340,112 S | 10/1993 | Zeman |
| 5,265,959 A | 11/1993 | Meltzer |
| 5,302,028 A | 4/1994 | Carey |
| 5,304,003 A | 4/1994 | Winninger |
| 5,309,899 A | 5/1994 | Ginsberg |
| 5,364,343 A | 11/1994 | Apolet et al. |
| 5,527,275 A | 6/1996 | Ginsberg |
| 5,662,605 A | 9/1997 | Hurwitz |
| 5,685,851 A | 11/1997 | Murphy et al. |
| 5,772,616 A | 6/1998 | Competiello et al. |
| 5,944,711 A | 8/1999 | Pender |
| 5,967,409 A | 10/1999 | Benedict |

* cited by examiner

Primary Examiner—Chen-Wen Jiang
(74) Attorney, Agent, or Firm—Wall Marjama & Bilinski LLP

(57) ABSTRACT

A body cavity irrigation system includes a housing having at least one interior chamber which is connectable to a faucet or other continuous fluid supply which delivers liquid under pressure through an inlet port. A discharge port of the housing is fluidly interconnected to an irrigation syringe having an actuable valve to control the dispensing of liquid from the housing to a body cavity through a discharge opening under controlled pressure. The liquid being dispensed can be monitored to ensure that the liquid is at an preferred temperature for effectively cleaning the body cavity without patient discomfort, the housing including an antiscald valve which prevents liquid above a predetermined temperature from being dispensed and in which at least one indicator indicates to the user that the liquid is above a second predetermined temperature whereby the first and second temperatures define a suitable temperature range. The system removes discharged water from the body cavity through an insertion tip of the syringe along a return path extending to the housing which includes a venturi which removes the discharged water.

42 Claims, 5 Drawing Sheets

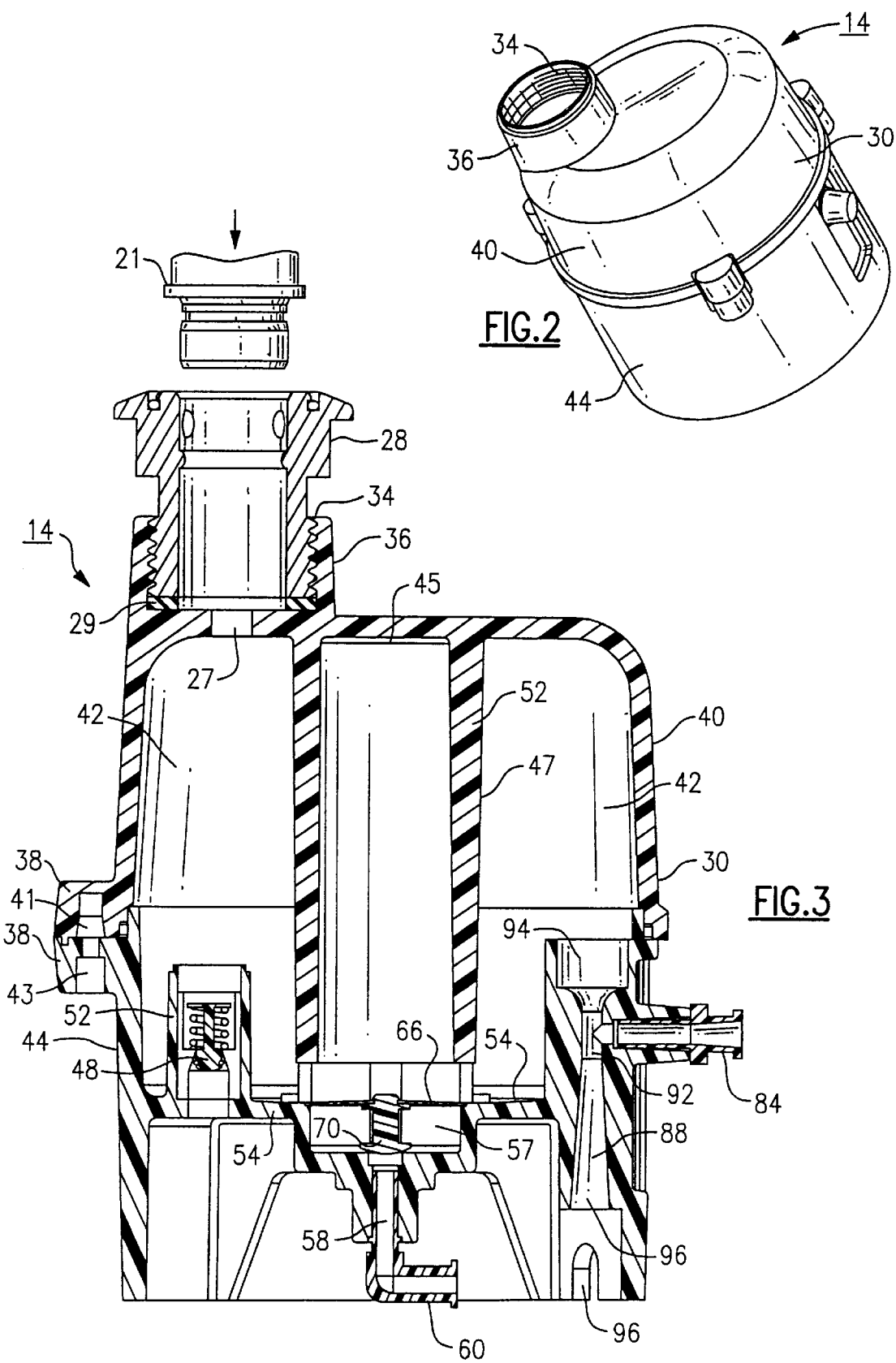

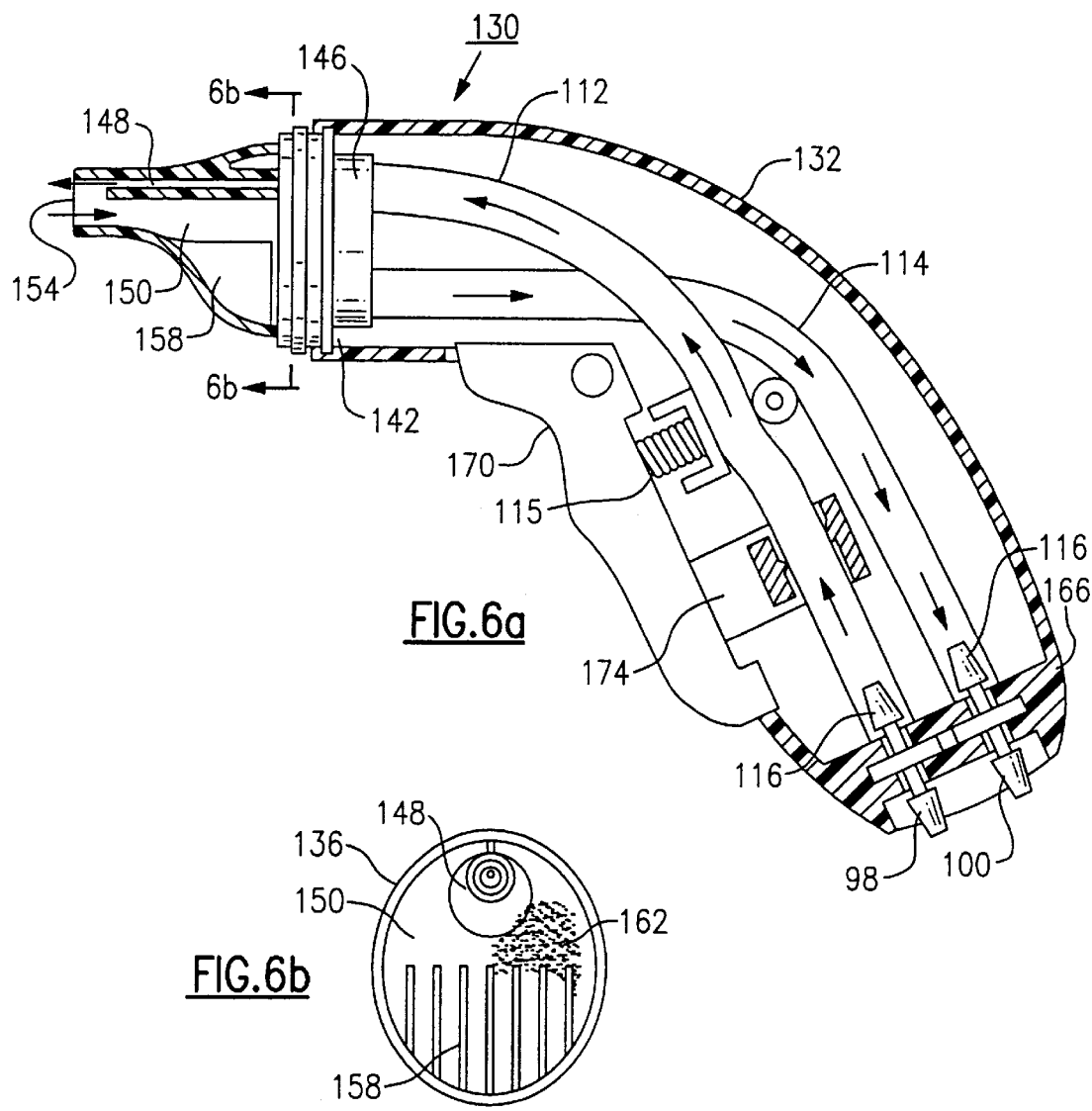
FIG.6a
FIG.6b
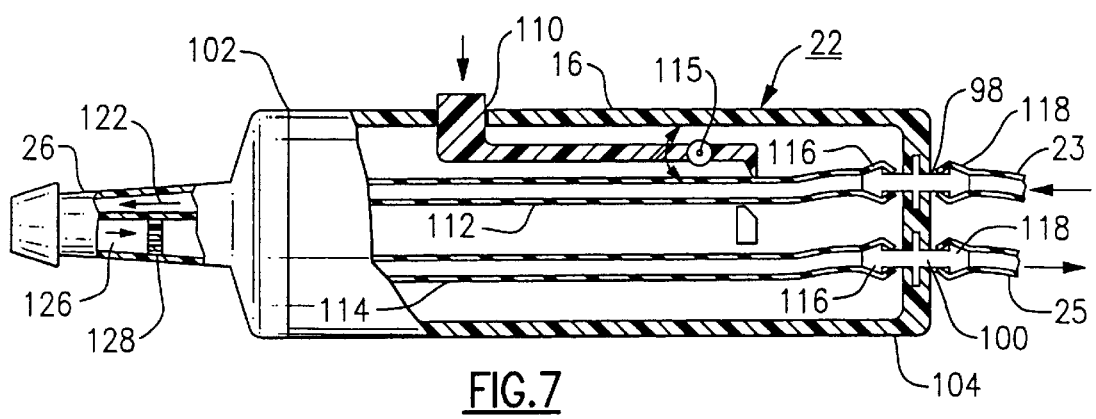
FIG.7

BODY CAVITY IRRIGATION SYSTEM

FIELD OF THE INVENTION

The invention relates to a system for injecting water or other fluid into a human body cavity, such as an ear, for cleaning thereof More specifically, the invention is directed to a body cavity irrigation system which allows user/patient monitoring to ensure efficacy of a cleaning procedure and that water of an optimal temperature is delivered continuously to a body cavity of interest. Further, the system conveniently collects discharged water from the body cavity.

BACKGROUND OF THE INVENTION

Irrigation syringes are known for cleaning human body cavities. For example, such devices can be used for routinely cleaning the ears of a patient. Most commonly, a flexible bulb is fitted to a nozzle through which fluid (water) is discharged into the ear canal of a patient.

Bulb-type devices have several drawbacks. First, the bulb capacity limits the usage of the device since the bulb contains a relatively small quantity of water. Often, and to fully irrigate a patient's ear, the bulb may have to be refilled a number of times.

Second, the pressure of the water exiting the nozzle and impinging upon the ear canal can not be readily controlled in a reliable manner. This lack of control produces variable results and can in turn, cause pain and injure a patient due to the sensitivity of the tympanic membrane.

Other known irrigation devices incorporate mechanical pumps which interconnect a fluid reservoir with the nozzle. These devices are capable of producing pulsating streams of ejecting water from the nozzle opening for a sustained period of time. Besides being rather bulky and cumbersome, the above devices produce both vibration and noise which are associated with mechanical pumps. Each result is annoying and undesirable in a doctor's office or similar setting. A further consideration with these devices is that the volume of the fluid reservoir, though greater than that of the flexible bulb-type devices, must also be refilled at periodic intervals.

In more recent advances, an irrigation-based ear wash device as described by U.S. Pat. No. 5,685,851, to Murphy et al, the entire contents of which are herein incorporated, includes a pressure regulator unit (a housing) having an inlet port which is fluidly connected to a faucet and a discharge port which is connected to an irrigation syringe. The irrigation syringe is hand-grippable and includes a push button control which selectively restricts the flow of liquid from the pressure regulator unit. The pressure regulator unit of this device permits connection to a continuous water source and includes a number of features, including a flow limiting orifice in a supply chamber, a defined air buffer, and a check valve, which effectively controls the pressure of water supplied by the faucet to produce a smooth and constant flow to the irrigation syringe.

At least two problems exist using any of the above described irrigation systems. A first probe relates to collection of the waste water after it has been discharged by the syringe. In the majority of prior art devices, such as described in U.S. Pat. No. 989,839, a basin is used to collect the waste water. If the basin is not used, then the patient must be irrigated in the vicinity of a sink in order to avoid spillages and further usually require the use of towels, drapes, and other accessories to attend to the discharged water. Using either method, the collection of waste water from a cleaning procedure is both tedious and time consuming, as well as inefficient.

A second problem long encountered in the field pertains to the temperature of water being discharged into the body cavity, especially in those systems that utilize a continuous water supply. Water which is too hot can create discomfort and in other cases could seriously injure the patient. It has further been determined that water which is too cold will not allow optimal cerumen removal. It has been determined that optimal removal is achieved using water which is at approximately body temperature.

Moreover, there appears to be no known irrigation system to date which can effectively and continuously deliver a fluid to a body cavity under controlled or regulated high pressure which further effectively solves each of the long standing problems that are noted above.

SUMMARY OF THE INVENTION

It is a primary object of the present invention to alleviate the above noted problems as encountered by prior art devices.

It is a further object of the present invention to provide a body cavity irrigation system having temperature controls which more reliably assures that water dispensed into a body cavity, such as the ear, permits cleaning at a comfortable near optimal temperature.

It is a further object of the present invention to provide an ear wash or other body cavity irrigation system that is capable of both delivering water continuously under pressure and removing discharged water away from the cavity without requiring cumbersome mechanical pumps or similar apparatus and precluding the use of drapes, basins, towels, and the like.

It is yet another primary object of the present invention to provide feedback to a user and/or patient such that either can effectively monitor the progress of a cleaning procedure.

It is yet a further object of the present invention to provide an ear wash or other body cavity irrigation system which is easy to use and operate repeatably.

It is yet a further object of the present invention to provide an irrigation system which is relatively inexpensive in terms of manufacture and which is simple and efficient in operation.

Therefore, and according to a preferred aspect of the invention, there is provided an irrigation system for cleaning a body cavity of a patient, said system comprising:

a housing fluidly connected to a liquid source through an inlet port, said housing further having at least one interior chamber and a discharge port;

a handpiece connected to the discharge port of said housing, said handpiece having an actuable control element to control the dispensing of liquid from said liquid source into a body cavity of the patient through a discharge opening; and means for delivering liquid to the discharge opening of said handpiece which is of a suitable temperature for effectively cleaning the body cavity without discomfort.

According to the present invention, the delivering means includes means for assuring that liquid exceeding a first predetermined temperature is not dispensed from the housing. In a preferred embodiment, an anti-scald valve is provided including a metallic disc-like element formed from a temperature reactive material.

If the temperature of water impinging upon the disc-like element exceeds the first predetermined temperature, the disc-like element is caused to move from a first position to a second position to effectively block the flow of liquid from the housing to the handpiece and eliminate the possibility of dispensing water that is too hot and could cause injury to the patient.

In addition, at least one indicator is also provided to indicate when liquid which has been discharged from the housing exceeds a second predetermined temperature to indicate an appropriate temperature range for effective cleaning, e.g., cerumen removal. Preferably, the indicator(s) is composed of or at least partially coated with a thermally reactive material which changes color when water exceeds a second predetermined temperature. The indicator can be provided at the insertion tip or anywhere along the fluid delivery path.

An advantageous feature of the above described irrigation system, as described, is that liquid which is too hot and can cause injury is prevented from being discharged from the housing by an anti-scald valve. Furthermore and in the event the water passing through the discharge port of the housing is too cold, the indicator adjacent the handpiece indicates when the liquid has exceeded a second predetermined temperature, indicating that the temperature of the liquid is less than the first predetermined temperature and is at a temperature which is most effective for use and comfortable for the patient. In this manner, the user can monitor when the syringe contains liquid to be dispensed which has the optimum temperature.

According to another preferred aspect of the present invention, there is provided a system for cleaning a body cavity of a patient, said system comprising:

a housing fluidly connected to a liquid supply through an inlet port, said housing further including a plurality of interior chambers and a discharge port;

a handpiece fluidly interconnected to the discharge port of said housing, said handpiece having an actuable control element to control the dispensing of liquid from said liquid supply into the ear of the patient through a discharge opening;

an insertion tip having at least one tip opening attached to said handpiece and aligned with said discharge opening, said insertion tip sized to be fitted a predetermined distance into the ear of a patient; and means for circulating liquid discharged into the ear of the patient through said insertion tip along a return path extending between said tip and said housing.

Preferably, the insertion tip includes a pair of cavities including a first cavity through which liquid is discharged into the ear from the discharge port of the housing and a second cavity through which liquid is recirculated to the housing along a return path. A pair of fluid channels are defined within the interior of the handpiece; a first channel in fluid communication between the discharge port of the housing and the first cavity of the insertion tip and a second channel in fluid communication between a return chamber of the housing and the second cavity of the insertion tip.

The liquid circulation means includes a return chamber provided in said housing and venturi means for drawing liquid discharged into the ear through the second cavity of the insertion tip and along a return path.

The venturi means includes a converging-diverging nozzle disposed in the return chamber, the return chamber further including a suction port fluidly interconnected with the handpiece along the return path.

Preferably, the insertion tip is disposable and can be made from a transparent material. The insertion tip can also be composed of or be coated with a thermally reactive material which changes color depending on the temperature of water in the tip.

An advantage of the present irrigation system is that the user can safely determine when to optimally dispense water for cleaning the ear or other body cavity.

A further advantage of the present system is that discharged liquid can be reliably and continually circulated to a sink or basin without the need for mechanical or electrical pumps or the need to refill the fluid source.

A further advantage of the present system is that it is more convenient to use than prior known devices since discharged water can be collected without the need of drapes, towels, or the like or otherwise requiring the patient to use a basin.

Yet another advantage of the present system is that a cleaning procedure performed using the system is simpler and more time efficient. Furthermore, the system provides lower patient risks in terms of both pressure and temperature while permitting continuous dispensing of water throughout a procedure.

Still another advantage provided by the herein described system is that the user or patient can monitor the efficacy of the cleaning procedure, for example, by examining a cerumen-catching filter of the insertion tip.

These and other objects, features, and advantages will be more apparent from the following Detailed Description which should be read in conjunction with the accompanying drawings.

BRIEF DESCRIPTION OF THE DRAWINGS

FIG. 2 is an enlarged top perspective view of the housing of the irrigation system of FIG. 1;

FIG. 3 is a side elevational view of the housing of FIGS. 1 and 2, taken in section;

FIG. 6(a) is a sectional view of an irrigation syringe for use in the irrigation system according to a selected embodiment of the invention;

FIG. 6(b) is a side view taken in section through lines 6(b)–6(b) of the irrigation syringe of FIG. 6(a) illustrating the interior of the insertion tip; and FIG. 7 is a sectional view of an irrigation syringe according to another embodiment of the present invention.

DETAILED DESCRIPTION

The following description specifically relates to an ear wash or irrigation system in accordance with certain preferred embodiments. It will, however, be readily apparent to one of sufficient skill in the field that there are many variations and modifications possible which embody the inventive aspects that are described and claimed herein. For example, and though the present device is described in terms of cleaning the ears, it should be readily apparent that the inventive concepts of the system can be also be applied to the cleaning of other body cavities, including but not limited to the anus, vagina, nose, and mouth. Furthermore, the system can also be used for other suitable purposes, such as the irrigation of wounds. In addition, terms are used throughout the description which provide a frame of reference with respect to the accompanying drawings, such as "top", "bottom", "lower", "upper", "distal", "proximal" and the like. These terms are not intended to be limiting of the present invention as claimed.

Figure 1:
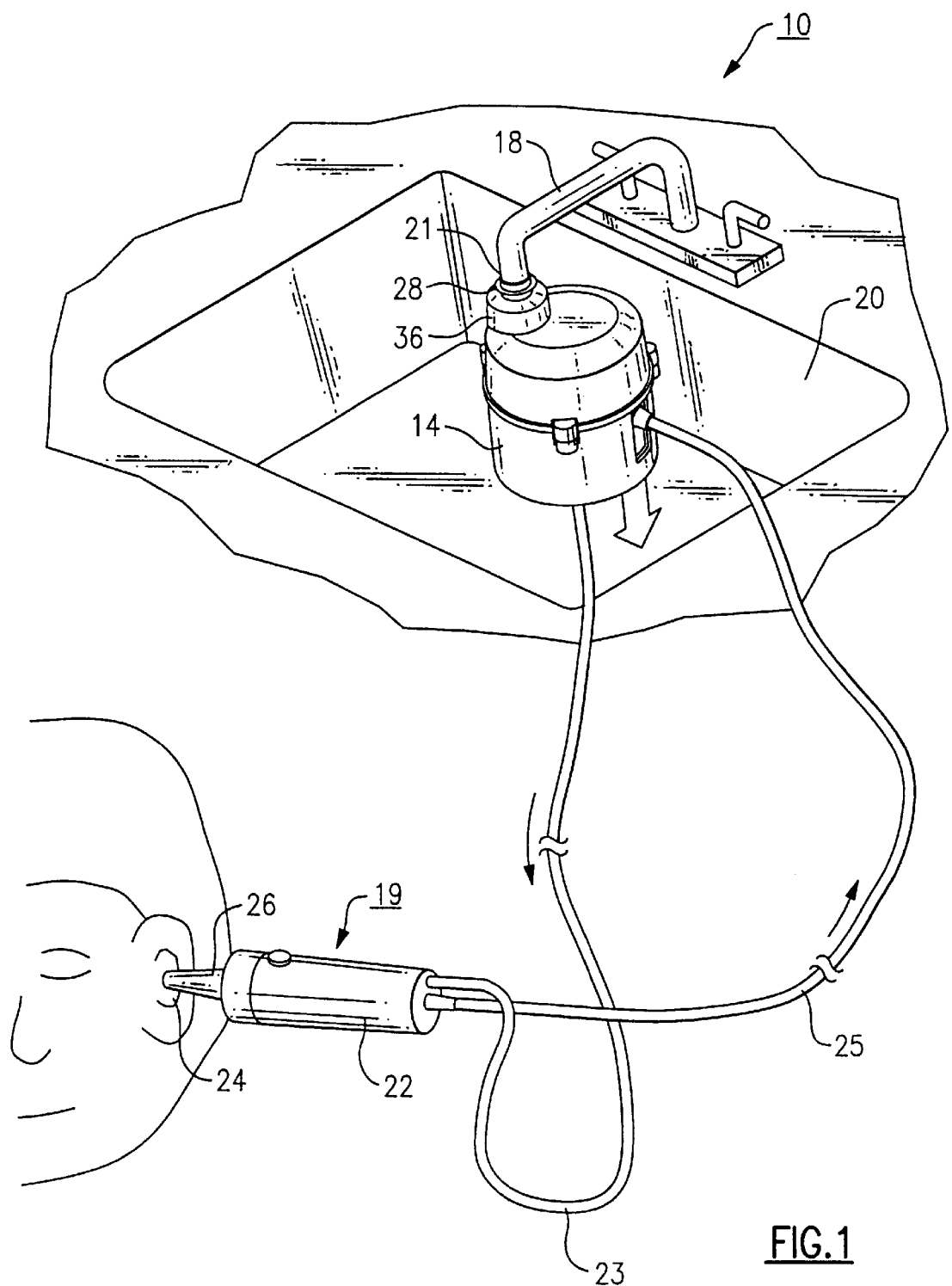
FIG. 1 is a perspective view of a body cavity irrigation system made in accordance with a preferred embodiment of the present invention.

Turning to FIG. 1, the irrigation based ear-wash system 10 includes a pressure regulator unit or housing 14 which is connected to a faucet 18 or other suitable continuous fluid supply that delivers liquid under pressure. The housing 14 is further connected to an irrigation syringe 19. In brief, the irrigation syringe 19 includes a handpiece 22 which is connected to the housing 14 by means of an inlet line 23 which delivers liquid from the housing to the handpiece 22 and a return line 25 through which discharged liquid is collected and then eliminated into a sink 20. The handpiece 22 shown in this FIG. includes an interfaced insertion tip 26 which is releasably attachable to the distal end thereof and is capable of being inserted a predetermined distance into the ear canal 24 of a patient. Details relating to each of the components of the irrigation system 10 are now described in greater detail, beginning with the housing 14.

Referring to FIGS. 1–4, the housing 14 includes a two-piece body 30 including an upper housing half 40 and a lower housing half 44, each being made from a liquid impermeable material such as an injection molded thermoplastic, such as ABS, or other suitable material. Each of the housing halves 40, 44 include at least one tab 38, each tab including an opening 41, 43, respectively, for retaining suitable fasteners (not shown) in order to define, when assembled, a fluid tight seal. It should be noted, for purposes of this discussion, that alternative mechanical attachment techniques, such as ultrasonic welding, adhesives, and other known fastening arrangements can be utilized so long as an effective fluid tight seal is achieved between the housing halves.

The upper housing half 40 includes an upper inlet port 36 having a plurality of internal threads 34 which permit connection through means of a sealed coupling 28 to the faucet 18 through an adapter 21, the coupling extending from the top of the housing body 30 and sealed therewith using a gasket 29.

A flow limiting orifice 27 is disposed in relation to the upper inlet port 36 of the housing 14, the orifice having a diameter which is substantially smaller than that of the upper inlet port in order to smooth out pressure fluctuations from the water supply and to provide a more steady fluid flow.

Referring more specifically to FIG. 3, the interior of the assembled housing 14 includes a pair of interconnected fluid chambers 42, 56. An outer chamber 42 is aligned with and is in fluid communication with the flow limiting orifice 27, the outer chamber 42 extending peripherally about an inner or center chamber 56. The inner chamber 56 is substantially defined by a hollow cylindrical portion 47 extending downwardly from a top interior surface 45 of the upper housing half 40. Each of the outer and inner chambers 42, 56 include a defined headspace permitting a volume of liquid to be stored therein. Preferably, the hollow cylindrical portion 47 of the inner chamber 56, as shown in FIG. 3, is formed such that in operation, described in greater detail below, an air buffer or cushion 59 is created at the upper end thereof. This air buffer 59 is produced based in part on the flow limiting orifice 27 and other features within the housing 14 described in greater detail below. In brief, however, the buffer 59 provides a dampening effect in order to smooth out any pressure fluctuations caused by variations in the supply water pressure. Additional details relating to the buffer 59, the flow limiting orifice 27 and the faucet adapter 21 are provided in U.S. Pat. No. 5,685,851, previously incorporated by reference above in its entirety. A bottom interior surface 54 of the lower housing half 44 includes a center recess 57 defining the bottom of the center chamber 56. A flow channel 58 extends downwardly from the center recess 57 to a discharge port coupling 60, the coupling being sized to receive one end of the inlet line 23, FIG. 1, which extends to the handpiece 22.

Referring to FIGS. 3–5(b), a valve assembly 62 is positioned within the center recess 57 of the inner chamber 56, the valve assembly including a substantially annular bimetallic disc element 66 which is disposed within an upper annular shoulder 65 of the recess. It should be noted in passing that though the preferred embodiment includes an annular disc element, this element can assume other geometries. The bimetallic disc element 66 includes a center opening 68 having attached therein an engagement end 72 of a plunger-like element 70, the element having a curved bottom portion 75 which is sized to fit in sealing engagement in the entrance of the flow channel 58. The bimetallic disc element 66, is preferably made from at least two metallic materials, each material having specific thermal expansion characteristics which causes the disc element 66 to be movable between a first curved shape, shown more particularly in the enlarged FIG. 5(a), and a second curved shape, shown more particularly in the enlarged FIG. 5(b), depending on the temperature of liquid impinging thereupon. The disc element 66 is caused to "pop" or trip to the second curved shape, FIG. 5(b), when the temperature of liquid impinging on the disc element 66 has exceeded a first predetermined temperature. Such elements 66 are commercially manufactured by Demaich Industries, Inc., among others.

According to this embodiment, the first predetermined temperature $T_1$ is about 105 degrees F., though it will be readily apparent that this particular parameter can easily be varied. The "popping" of the disc element 66 is literally instantaneous and when the disc element is caused to assume the second curved shape, the attached plunger-like element 70 is pushed downwardly into a seated position within the entrance of the flow channel 58, preventing high temperature liquid from passing to the handpiece 22. The sealing of the plunger-like element 70 prevents the discharge of excessively hot water which would, at a minimum, produce discomfort for the patient as well as possible injury.

Referring back to FIGS. 3 and 4, the housing 14 further includes a substantially horizontal suction port 84 extending from a side exterior wall of the housing body 30 which transversely enters into a vertically disposed venturi 88. The venturi 88 has a tubular construction including a narrowed intermediate entrance 92 at the suction port 84 between an inlet end 94 disposed in relation to the outer chamber 42 oppositely from the inlet port 36 side of the housing 14, and a opposing divergent discharge outlet 96 arranged to discharge liquid from the bottom of the housing. The specific location of the venturi does not affect the functions of the venturi 88 which will be described in greater detail below, though the overall theory of their operation are well known in the field and should require no further discussion.

Finally, the housing 14 further includes a check valve 48 disposed at the bottom of the outer chamber 42, the valve being disposed within a hollow cylindrical portion 52 extending upwardly from the bottom interior surface 54. In brief, the check valve 48 is set to open to allow liquid to flow out of the housing if the supply pressure exceeds a predetermined pressure. A similar valve is described in U.S. Pat. No. 5,685,851, previously incorporated by reference herein.

The irrigation syringe 19 in accordance with a first embodiment of FIG. 1, is herein described in greater detail with reference to FIG. 7. According to this embodiment, the irrigation syringe 19 includes a handpiece having a substantially cylindrical body 16 and a disposable insertion tip 26 that is releasably mounted to a distal end 102 thereof. Preferably, the handpiece 22 and the insertion tip 26 are each formed from an injection molded plastic, the tip having a substantially frusto-conical shape which permits positioning a predetermined insertion distance into the ear canal 24, FIG. 1, of a patient. More preferably, the insertion tip 26 according to the present embodiment is made from a transparent plastic material for reasons which are detailed below.

As shown, the majority of the handpiece 22 and the insertion tip 26 are hollow. The handpiece 22 includes a pair of couplings 98, 100 at a proximal end 104 as well as a corresponding pair of fluid channels 112, 114 extending over the length of the hollow interior thereof. Each of the couplings 98, 100 are hollow and include a pair of opposing barbs 116, 118. One end of each of the fluid channels 112, 114 are attached to one set of barbs 116, while the remaining barbs 118 accept corresponding ends of the inlet line 23 and return line 25, each partially shown in FIG. 7.

The remaining ends of the fluid channels 112, 114 are similarly attached to couplings (not shown) provided at the proximal end of the insertion tip 26. The insertion tip 26 includes a pair of adjacent cavities, 122, 126 extending through the length thereof. As such, the inlet line 23, handpiece fluid channel 112, and insertion tip cavity 122 define a supply or delivery fluid path extending between the housing 14 and the body cavity of interest, while the return line 25, handpiece fluid channel 114, and insertion tip cavity 126 define a suction or return path extending from the insertion tip 26 to the suction port 84 and venturi 88. Preferably, a filter 128 disposed within the insertion tip return cavity 126 prevents loose cerumen from being returned to the housing 14 and further provides feedback of the efficacy of the cleaning procedure due to the transparent insertion tip.

An actuable valve or control element, such as a pushbutton 110, provided on the exterior of the handpiece 22 permits the inlet fluid channel 112 to be clamped upon depression thereof in order to prevent liquid from being dispensed. According to this embodiment, a torsion spring 115 biases the pushbutton 110 upon a second activation to a neutral or unengaged position, allowing fluid to flow. It should be readily apparent to one of ordinary skill in the field that many other pushbutton or actuable valve designs can be substituted to perform the same functions.

According to this embodiment, at least a portion of the insertion tip 26 is composed of or is coated with a temperature reactive material such as a thermochromic plastic or a coating, such as those manufactured by GE Plastics or Hallcrest, Inc., among others, in which the material changes color when a predetermined temperature is exceeded. Alternately, any portion of the delivery path, such as, for example, inlet coupling 98, can include a similar type of indicator.

Prior to describing the overall operation of the irrigation device, a second embodiment of an irrigation syringe 130 is herein described with reference to FIGS. 6(a) and 6(b). For the sake of convenience, similar parts are herein labeled with the same reference numerals. As in the preceding, the irrigation syringe 130 includes a handpiece 132 and an insertion tip 136 which is releasably attached to a distal end 138 of the handpiece. In this embodiment, the handpiece 132 is defined by a handgrippable pistol-shaped body made preferably from a lightweight injection-molded plastic and includes a distal opening 142 accessing an engagement portion which recieves the insertion tip 136.

The insertion tip 136 according to this embodiment is formed from a transparent injection-molded plastic, at least a portion of which is composed of or is coated with a thermally reactive material which changes color if a predetermined temperature is exceeded, as previously described in connection with the embodiment of FIG. 7. The insertion tip 136 is substantially hollow and includes adjacent cavities 148, 150, which when assembled to the handpiece 132 are aligned with and positioned through barbs (not shown) or other means in fluid communication with the distal ends of respective supply and return fluid channels 112, 114. The inlet cavity 146 of the insertion tip 136 is relatively narrow extending to a distal tip opening 154. The return cavity 150 is preferably wider than the inlet cavity 146 and includes a filter 158 designed to trap removed cerumen 162.

The proximal ends of the flexible fluid channels 112, 114 are attached to respective barbs 116 of inlet and outlet couplings 98, 100 provided at the proximal end 166 of the handpiece 132 and in fluid communication with the inlet and return lines 23, 25, FIG. 1, respectively.

The handpiece 132 includes a trigger 170 which enables a clamp 174 to pinch off the flexible inlet fluid channel 112, the clamp being biased by a torsion spring 115. Depression of the trigger 170 releases the pressure of the clamp 174 upon the fluid channel 112 to selectively permit fluid flow from the housing 14 for dispensing thereof.

Referring now in general to the Figs., and in operation, the housing 14 is initially connected to the faucet 18 by means of coupling 28 and adapter 21, partially shown in FIG. 3. When the faucet 18 is turned on, liquid advances into the interior of the housing 14 via the flow limiting orifice 27 into the outer chamber 42. As shown more completely in FIGS. 4, 5(a), and 5(b), water fills the outer chamber 42 and advances into the inner chamber 56. As the water is continually being supplied to the housing 14, water is also being continually discharged through the discharge outlet 96 of the venturi 88 into the sink 20, FIG. 1, particularly prior to the dispensing of liquid from the irrigation syringe 19. As water is advanced into the inner chamber 56, water is also being continually advanced across both major sides of the annular disc element 66, the annular shoulder 65 further including opposing bypass slits 64, shown in FIG. 5(a) only, which allows water to pass into the center recess 57 and into the flow channel 58, discharge port coupling and supply line 23. The design of the flow limiting orifice 27, the venturi 88, and the check valve 48 allow formation of the air buffer 59, each further combining to effectively control or regulate the supply liquid pressure from fluctuations and the like.

The temperature monitoring features of the present invention are herein described in terms of the operation of the described system. Fluid (e.g., water) having a temperature below a first predetermined temperature which enters the lower recess 57 of the inner chamber 56 will pass into the flow channel 58 and into the supply line 23 through the irrigation port coupling 60. The water then passes through the supply line 23 to the handpiece 22. When the faucet 18 is initially opened, the liquid may not yet be warm enough for comfortable use in irrigating the ear of a patient. Therefore and according to one embodiment, the inlet coupling 98 which is composed of or at least partially coated with a thermally reactive material, as described above in connection with the insertion tips of FIGS. 6(a), 6(b), and 7 of the handpiece 22 will display a first color (e.g., blue) which is indicative that the water temperature is below a second predetermined temperature. When the water temperature, as sensed by the inlet coupling 98, reaches the second predetermined value (e.g., about 95 degrees F.), the color of the coupling then changes to a second color (e.g. green) indicating to the user that the water is at an optimum or near optimum temperature for dispensing at which time the irrigation procedure can begin.

Figure 5A:
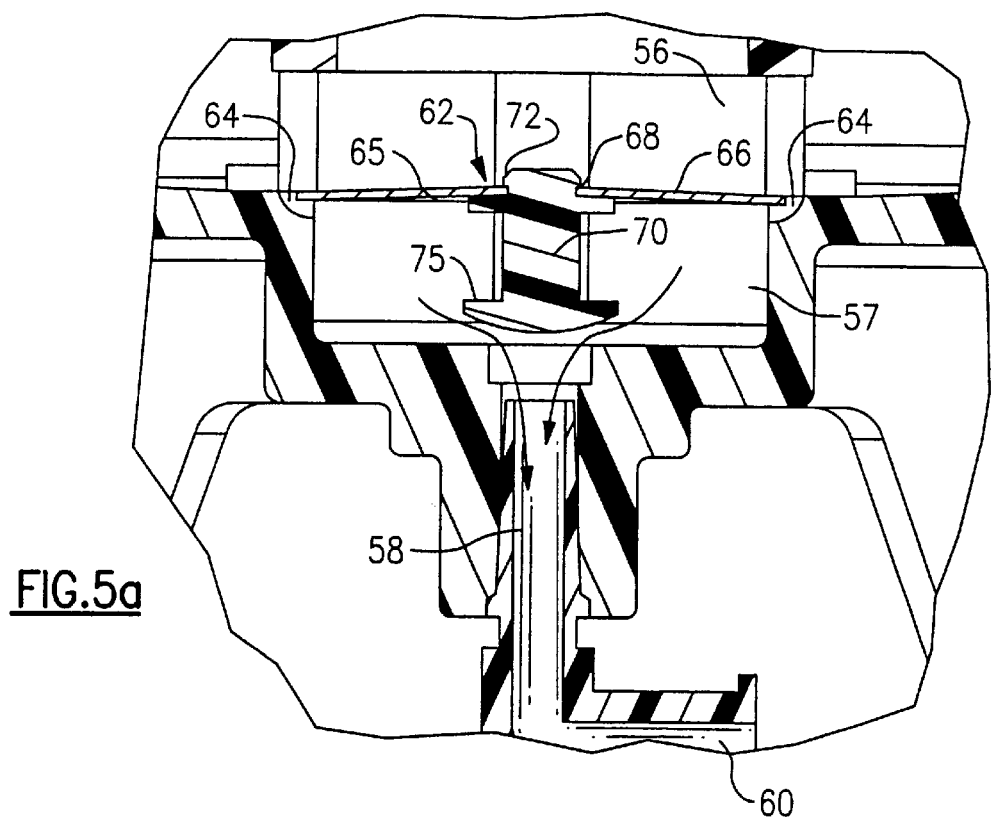
FIG. 5(a) is an enlarged partial sectional view of the housing interior including an anti-scald valve according to the present invention, the valve being in an open position.
Figure 5B:
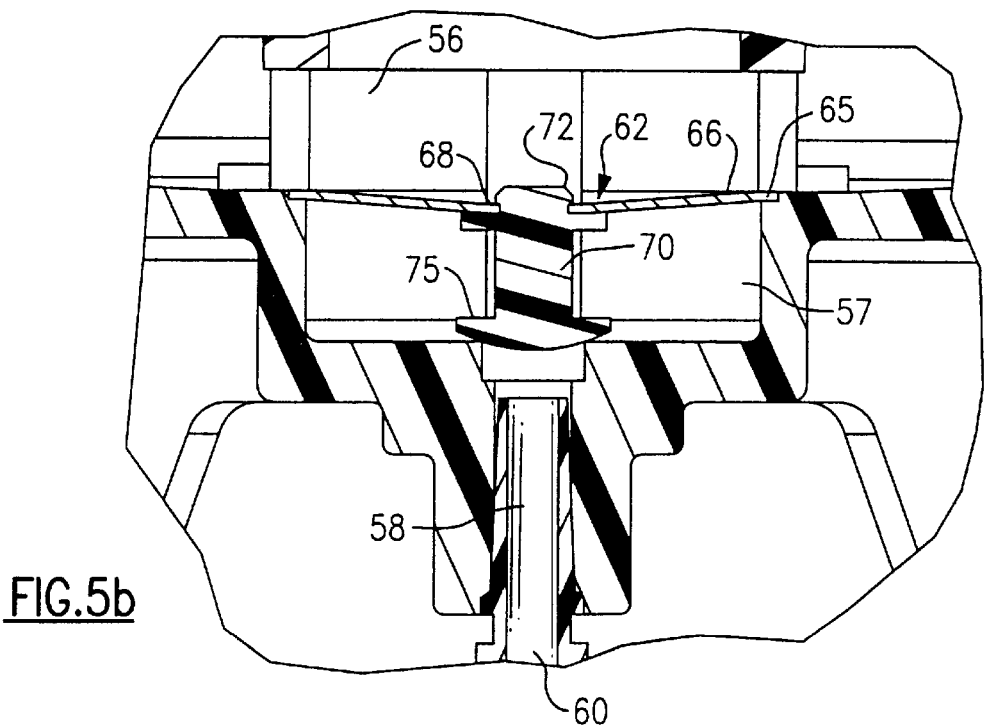
FIG. 5(b) is the enlarged view of FIG. 5(a) showing the anti-scald valve of FIG. 5(a) in a closed position.

Through the use of the pushbutton 110, the user can selectively control the dispensing of liquid stored in the housing 14 based on the color of the thermally sensitive inlet coupling 98 to ensure that water to be dispensed is at a temperature which is optimum for effectively removing cerumen. In the meantime, the bimetallic disc element 66 within the housing 14 acts as an anti-scald valve to prevent excessively hot liquid from being dispensed as shown in FIG. 5(b) in which the plunger-like element 70 is caused by the popping of the disc element to effectively block the flow channel 58. In this manner, the temperature of water can be effectively monitored to ensure only water within a specified range (e.g., 95–105 degrees F.) is dispensed.

Figure 4:
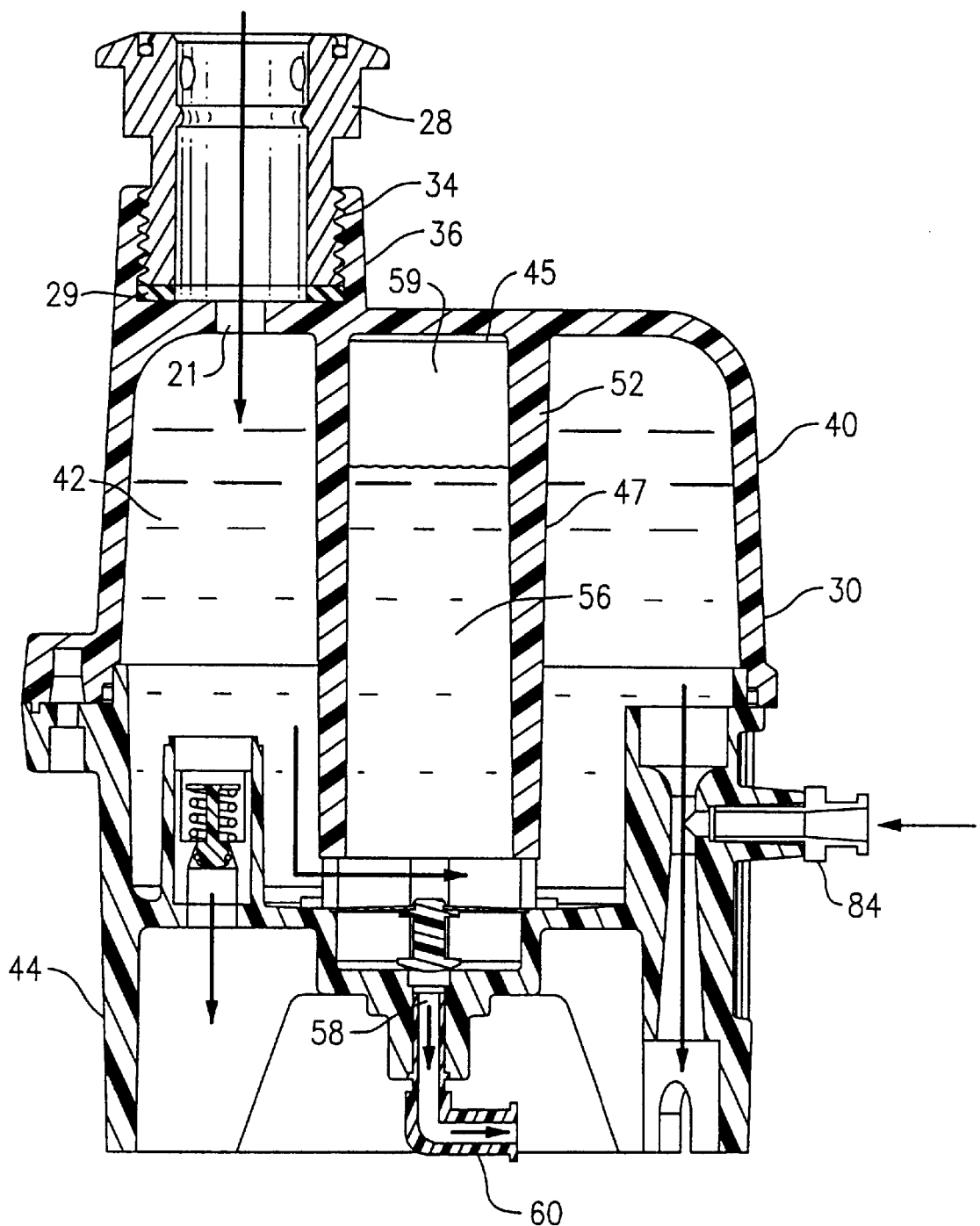
FIG. 4 is the side elevational view of FIG. 3, depicting the flow of liquid to and from the housing.

Referring more specifically FIGS. 4 and 7, liquid is dispensed into the ear canal of the patient with the liquid dispensed into the ear from supply cavity 122 flushing cerumen through the filter 128, with the waste water being sucked back into the tip via suction cavity 126, due to the negative pressure differential created by the venturi 88. A filter or trap 128, FIG. 7, provided within the insertion tip 26 screens cerumen and other particulates to prevent clogging of the suction line. The filter 128 and the transparent nature of the insertion tip 26 also provides visual feedback to the patient and the physician regarding the efficacy of the cleaning procedure. Excess liquid is therefore discharged directly into the sink 20, FIG. 1, through the discharge outlet 96 of the venturi 88.

PARTS LIST FOR FIGS. 1–7

| | |
|---|---|
| 10 | irrigation system |
| 14 | housing |
| 16 | cylindrical body |
| 18 | faucet |
| 19 | irrigation syringe |
| 20 | sink |
| 21 | adapter |
| 22 | handpiece |
| 23 | inlet line |
| 24 | ear canal |
| 25 | return line |
| 26 | insertion tip |
| 27 | flow limiting orifice |
| 28 | coupling |
| 29 | gasket |
| 30 | body |
| 34 | internal threads |
| 36 | upper inlet port |
| 38 | tabs |
| 40 | upper housing half |
| 41 | opening |
| 42 | outer chamber |
| 43 | opening |
| 44 | lower housing half |
| 45 | top interior surface |
| 47 | hollow cylindrical portion |
| 48 | check valve |
| 52 | hollow cylindrical portion |
| 54 | bottom interior surface |
| 56 | inner chamber |
| 57 | center recess |

-continued

PARTS LIST FOR FIGS. 1–7

| | |
|---|---|
| 58 | flow channel |
| 59 | air buffer |
| 60 | irrigation port coupling |
| 62 | valve assembly |
| 64 | bypass slits |
| 65 | annular shoulder |
| 66 | bimetallic disc-like element |
| 68 | center opening |
| 70 | plunger-like element |
| 72 | engagement end |
| 75 | curved bottom portion |
| 84 | suction port |
| 88 | venturi |
| 92 | narrowed entrance |
| 94 | inlet end |
| 96 | discharge outlet |
| 98 | coupling |
| 100 | coupling |
| 102 | distal end |
| 104 | proximal end |
| 110 | pushbutton |
| 112 | supply channel |
| 114 | suction channel |
| 115 | torsion spring |
| 116 | barb |
| 118 | barb |
| 122 | cavity |
| 126 | cavity |
| 128 | filter |
| 130 | irrigation syringe |
| 132 | handpiece |
| 136 | insertion tip |
| 138 | distal end |
| 142 | distal tip opening |
| 146 | engagement portion |
| 148 | inlet cavity |
| 150 | return cavity |
| 154 | distal tip opening |
| 158 | filter |
| 162 | removed cerumen |
| 166 | proximal end |
| 170 | trigger |
| 174 | clamp |

While the present invention has been particularly shown and described with reference to the preferred mode as illustrated in the accompanying drawings, it will be understood by one skilled in the art that various changes in detail may be effected therein without departing from the spirit and scope of the invention as defined by the claims.

We claim:

1. An irrigation system for cleaning a body cavity of a patient, said irrigation system comprising:

a housing fluidly connected to a liquid source through an inlet port, said housing further having at least one interior chamber, a discharge port, and means for preventing liquid which is greater than a first predetermined temperature from exiting said discharge port, wherein said liquid exit preventing means includes a valve assembly disposed in said housing, said valve assembly including at least one thin valve member formed from a bimetallic temperature responsive material which is movable between a first position and a second position when liquid exceeding the first predetermined temperature impinges directly thereupon to automatically prevent liquid exceeding the first predetermined temperature from being discharged from the housing to the handpiece;

a handpiece connected to the discharge port of said housing, said handpiece having an actuable control element to control the dispensing of liquid from said liquid source to a body cavity through a discharge opening; and means for delivering liquid from the discharge port to the discharge opening of said handpiece, said liquid delivering means including means for indicating when said liquid is greater than a second predetermined temperature, said second predetermined temperature being a suitable temperature for effectively cleaning the body cavity without patient discomfort.

2. An irrigation system according to claim 1, wherein at least a portion of the fluid travel path between the housing and the handpiece includes a thermally reactive material which changes from at least a first color to at least a second color when liquid having at least said second predetermined temperature passes through said portion.

3. An irrigation system according to claim 2, wherein said liquid delivering means includes a flexible channel fluidly interconnecting the discharge port of said housing and said handpiece, in which at least a portion of said channel includes said thermally reactive material.

4. An irrigation system according to claim 1, wherein said valve assembly is disposed adjacent the discharge port of said housing.

5. An irrigation system according to claim 1, wherein said thin valve member of said valve assembly is attached to a plunger, said plunger being sized to fit within the discharge port of said housing to block the discharge of liquid exceeding the first predetermined temperature when said thin valve member is caused to move to the second position.

6. An irrigation system according to claim 5, wherein said thin valve member of said valve assembly is a disc-like member which changes from a first shape in the first position to a second shape different from the first shape in the second position so as to engage the plunger and block the discharge port.

7. An irrigation system according to claim 1, wherein said handpiece is releasably attachable to the discharge port of said housing.

8. An irrigation system according to claim 1, wherein said handpiece includes an insertion tip having a discharge opening aligned with the discharge opening of said handpiece.

9. An irrigation system according to claim 8, wherein said insertion tip is releasably attachable to said handpiece.

10. An irrigation system according to claim 8, wherein said insertion tip is formed from a transparent material.

11. An irrigation system according to claim 8, wherein said insertion tip is formed from a colored material.

12. An irrigation system according to claim 8, wherein said insertion tip is disposable.

13. An irrigation system according to claim 1, wherein said liquid supply is a pressurized liquid supply.

14. An irrigation system according to claim 8, wherein said insertion tip is at least partially formed from a thermally reactive material which changes color depending on the temperature of the liquid in the tip.

15. An irrigation system according to claim 1, wherein the body cavity is the ear canal.

16. An irrigation system for cleaning a body cavity of a patient, said system comprising:
a housing fluidly connected to a liquid supply through an inlet port, said housing further including a plurality of interior chambers and a discharge port;
a handpiece fluidly interconnected to the discharge port of said housing, said handpiece having an actuable control element to control the dispensing of liquid from said liquid supply into a body cavity of a patient through a discharge opening;
an insertion tip having at least one tip opening attached to said handpiece and aligned with said discharge opening, said insertion tip sized to be fitted a predetermined distance into the body cavity of a patient; and
means for circulating liquid discharged into the body cavity through said insertion tip along a return path extending between said insertion tip and said housing.

17. An irrigation system according to claim 16, wherein said circulating means includes means for selectively actuating said circulating means.

18. An irrigation system according to claim 16, wherein said insertion tip includes a pair of cavities including a first cavity through which liquid is discharged into the body cavity from said discharge port of said housing and a second cavity through which liquid is recirculated to said housing along said return path.

19. An irrigation system according to claim 18, wherein said liquid circulation means includes venturi means for drawing liquid discharged into the body cavity through said second cavity of said insertion tip and along said return path to said housing.

20. An irrigation system according to claim 19, wherein said venturi means includes at least one converging-diverging nozzle disposed in a return chamber of said housing, said return chamber including a port fluidly interconnected with said handpiece.

21. An irrigation system according to claim 20, wherein said return chamber includes an outlet port for discharging the returned liquid from the housing.

22. An irrigation system according to claim 18, wherein said circulating means includes at least one filter disposed along said return path for trapping participate matter in the circulated liquid.

23. An irrigation system according to claim 22, wherein at least one filter is disposed in said second cavity of said insertion tip.

24. An irrigation system according to claim 16, wherein said handpiece includes a pair of fluid chambers within the interior of said handpiece, said pair of chambers including:
a first chamber in fluid communication between the discharge port of said housing and the first cavity of said insertion tip; and
a second chamber in fluid communication between a return chamber of said housing and the second cavity of said insertion tip.

25. An irrigation system according to claim 16, wherein said liquid supply is a faucet and said housing is disposed in a sink for receiving the discharged liquid exiting said housing through said outlet port.

26. An irrigation system according to claim 16, wherein said insertion tip is releasably attachable to said handpiece.

27. An irrigation system according to claim 16, wherein said insertion tip is made from a transparent material.

28. An irrigation system according to claim 16, wherein at least a portion of said insertion tip is made from a thermally reactive material which changes color depending on the temperature of liquid in the tip.

29. An irrigation system according to claim 16, wherein said body cavity is the ear canal.

30. An irrigation system according to claim 29, wherein said insertion tip is defined by a substantially frusto-conical shape for fitting a predetermined distance into an ear canal and forms a substantially sealed connection therewith.

31. An irrigation system according to claim 16, wherein said insertion tip is at least partially made from a colored material.

32. A method for cleaning a body cavity using an irrigation system, said irrigation system including a housing attachable to a liquid supply through an inlet port, said housing further having at least one interior chamber and a discharge port in fluid communication with a handpiece, said handpiece including means for selectively discharging liquid from said liquid supply through a discharge opening, said method including the steps of:

preventing liquid exceeding a first predetermined temperature from being delivered to said handpiece by placing a thin valve member between said inlet port and said discharge port within said housing, said thin valve member being made from a bimetallic temperature reactive material so as to cause said thin valve member to move from a first open position to a second closed position when liquid directly impinging on said thin valve member exceeds said first predetermined temperature;

indicating when liquid exceeding a second predetermined temperature which is less than the first predetermined temperature has been delivered to the handpiece; and discharging liquid after said indicating step, thereby ensuring only liquid of a suitable temperature enters the body cavity.

33. An irrigation syringe comprising:

a pressure regulator unit fluidly connected to a liquid supply;

a handpiece fluidly connected to said pressure regulator unit, said handpiece including means for selectively controlling the discharge of liquid from said liquid supply through a tip sized for insertion at least a predetermined distance into the body cavity of a patient, said tip including a first cavity, and a second cavity separate from said first cavity, each of said first and second cavities having an opening, wherein said first cavity is in fluid communication with a supply chamber of said pressure regulator unit and connected to said selective controlling means for discharging liquid through said opening and said second cavity is in fluid communication with a return chamber of said pressure regulator unit, said pressure regulator unit having means for circulating discharged liquid through said second cavity and along a return path to said pressure regulator unit.

34. An irrigation syringe according to claim 33, wherein said tip is releasably attachable to said handpiece.

35. An irrigation syringe according to claim 34, wherein said tip is disposable.

36. An insertion tip for an irrigation syringe, said syringe including a pressure regulator unit which is fluidly connected to a continuous liquid supply and a handpiece fluidly connected to said pressure regulator unit, said handpiece including means for selectively controlling the discharge of liquid from said liquid supply, said disposable tip being releasably attachable to said handpiece and sized for insertion at least a predetermined distance into the ear canal of a patient, said tip including a first cavity and a second cavity separate from said first cavity, each of said first and second cavities having an opening, wherein said first cavity is in fluid communication with a supply chamber of said pressure regulator unit and said second cavity is in fluid communication with a return chamber of said pressure regulator unit.

37. An insertion tip according to claim 36, wherein said tip is made from a transparent material.

38. An insertion tip according to claim 36, wherein said tip is disposable.

39. An insertion tip according to claim 36, including at least one filter disposed in said second cavity for capturing particulates from circulated liquid.

40. An insertion tip according to claim 36, wherein said tip is at least partially formed from a thermally reactive material which changes color depending on the temperature of liquid in the tip.

41. An insertion tip according to claim 36, wherein said tip is at least partially made from a colored material.

42. A method for cleaning the ear using an irrigation system, said irrigation system including a housing attachable to a liquid supply through an inlet port, said housing further having at least one interior chamber and a discharge port in fluid communication with a handpiece, said handpiece including means for selectively discharging liquid from said liquid supply through a discharge opening, said method including the steps of:

preventing liquid exceeding a first predetermined temperature from being delivered to said handpiece by placing a thin valve member between said inlet port and said discharge port within said housing, said thin valve member being made from a bimetallic temperature reactive material so as to cause said thin valve member to move from a first open position to a second closed position when liquid directly impinging on said thin valve member exceeds said first predetermined temperature;

indicating when liquid exceeding a second predetermined temperature has been delivered to the handpiece; and discharging liquid after said indicating step, thereby ensuring only liquid of a suitable temperature enters the ear.

* * * * *